(12) United States Patent
Orr

(10) Patent No.: US 8,377,893 B2
(45) Date of Patent: *Feb. 19, 2013

(54) HIGHLY PURIFIED ANTIENDOTOXIN COMPOUND

(75) Inventor: John D. Orr, Amesbury, MA (US)

(73) Assignee: Eisai R&D Management Co., Ltd., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 12/816,913

(22) Filed: Jun. 16, 2010

(65) Prior Publication Data

US 2011/0130353 A1     Jun. 2, 2011

Related U.S. Application Data

(63) Continuation of application No. 10/478,459, filed as application No. PCT/US02/16203 on May 22, 2002, now Pat. No. 7,759,323.

(60) Provisional application No. 60/293,012, filed on May 22, 2001.

(51) Int. Cl.
*A61K 31/7016* (2006.01)
*C07H 15/04* (2006.01)

(52) U.S. Cl. ............... 514/25; 536/21
(58) Field of Classification Search .......... 514/25; 536/17.1
See application file for complete search history.

(56) References Cited

U.S. PATENT DOCUMENTS

| 5,681,824 A * | 10/1997 | Christ et al. ............... 514/53 |
| 6,235,724 B1 | 5/2001 | Asai et al. |
| 6,861,512 B2 | 3/2005 | Lu et al. |
| 6,906,042 B2 | 6/2005 | McShane et al. |

FOREIGN PATENT DOCUMENTS

| EP | 0 172 581 A2 | 2/1986 |
| GB | 2220211 A | 1/1990 |
| JP | H7-304750 | 11/1995 |
| JP | H11-500442 | 1/1999 |
| JP | H11-506793 | 6/1999 |
| JP | 2000-502356 | 2/2000 |
| WO | WO 96/26205 | 8/1996 |
| WO | WO 96/39411 | 12/1996 |
| WO | WO 97/11708 | 4/1997 |
| WO | WO 97/30992 | 8/1997 |

OTHER PUBLICATIONS

John A. Dean, Analytical Chemistry Handbook, 1995 2.52-2.55.
Dean, Analytical Chemistry Handbook, 1995, 2.53-2.56; 4.71-4.79.
Dan, J.A. Analytical Chemistry Handbook, 1995, 2.52-2.56; 4.71-4.79.
Dean, Analytical Chemistry Handbook, 1995, 2.53-2.56; 4.66-4.67; 4.71-4.79.
Snyder et al., *Practical HPLC Method Development*, John Wiley & Sons 15-41, 1988.
Asai et al., *The Effect of the Membrane Fluidity on Pharmacokinetics for Lipid A analog E5531*, Drug Development and Industrial Pharmacy 26:383-390, 2000.
Snyder et al., *Practical HPLC Method Development*, Wiley: New York 1988, p. 32.

* cited by examiner

*Primary Examiner* — Eric S Olson
*Assistant Examiner* — Ganapathy Krishnan
(74) *Attorney, Agent, or Firm* — Buchanan Ingersoll & Rooney PC

(57) ABSTRACT

The invention provides compositions containing a highly purified antiendotoxin compound and methods of preparing and using such compositions.

11 Claims, 5 Drawing Sheets

HIGHLY PURIFIED ANTIENDOTOXIN COMPOUND

RELATED APPLICATIONS

This application is a continuation of, and claims priority from, U.S. application Ser. No. 10/478,459, filed Jun. 1, 2004, now U.S. Pat. No. 7,759,323 which, in turn claims priority under 35 U.S.C. §371 from PCT/US02/16203, filed May 22, 2002, which, in turn, claims priority under 35 U.S.C. §119 from U.S. Application Ser. No. 60/293,012, filed May 22, 2001. The contents of each of these applications are incorporated in their entireties by this reference.

BACKGROUND OF THE INVENTION

This invention relates to compositions containing a highly purified antiendotoxin compound and methods of preparing and using such compositions.

Since the 1930's, the increasing use of immunosuppressive therapy and invasive devices, as well as the increased incidence of antibiotic resistance in bacteria, have led to a gradual rise in the occurrence of sepsis and septic shock. Currently, the estimated incidences in the U.S. of sepsis and septic shock are 400,000 and 200,000 patients/year, respectively. This results in about 100,000 fatalities/year, making septic shock the most common non-coronary cause of death in hospital Intensive Care Units (ICUs). Currently, ICU therapy for septic shock is limited to antibiotic therapy, cardiovascular resuscitation, vasopressor/ionotrope therapy, and ventilatory support. This ICU care can cost up to $1,500/day and average a total of $13,000 to $30,000 per patient. Clearly, any therapy that can reduce the morbidity and cost for the care of sepsis/septic shock will be of great value.

It is likely that antibiotics themselves can worsen morbidity associated with sepsis; their bactericidal action can result in the release of endotoxin from gram negative bacteria, which is believed to induce many pathophysiological events such as fever, shock, disseminated intravascular coagulation (DIC), and hypotension. Consequently, medicines for the treatment of gram negative sepsis have been desired for some time, especially drugs capable of blocking endotoxin or cytokines derived from endotoxin-mediated cellular stimulation. To this end, various strategies for treatment have included administration of antibodies or other agents against lipopolysaccharide (LPS) or cytokines, such as TNF-α and interleukin-1. For various reasons, these approaches have failed.

While endotoxin itself exists in multiple molecular forms, the expression of many of the toxic properties of endotoxin is attributed to the highly conserved hydrophobic lipid A portion. An effective drug that acts as an antagonist to this conserved structure is known as E5564 (also known as compound B1287 and SGEA). This drug is described as compound 1 in U.S. Pat. No. 5,681,824, which is incorporated herein by reference. E5564 has the formula: (α-D-Glucopyranose, 3-0-decyl-2-deoxy-6-O-[2-deoxy-3-O-[(3R)-3-methoxydecyl)-6-O-methyl-2-[[(11Z)-1-oxo-11-octadecenyl)amino]-4-O-phosphono-β-D-glucopyranosyl]-2-[(1,3-dioxotetradecyl)amino]-,1-(dihydrogen phosphate), which can be provided as a tetrasodium salt. E5564 has a molecular weight of 1401.6.

SUMMARY OF THE INVENTION

The invention provides a composition including a compound, E5564, having the formula:

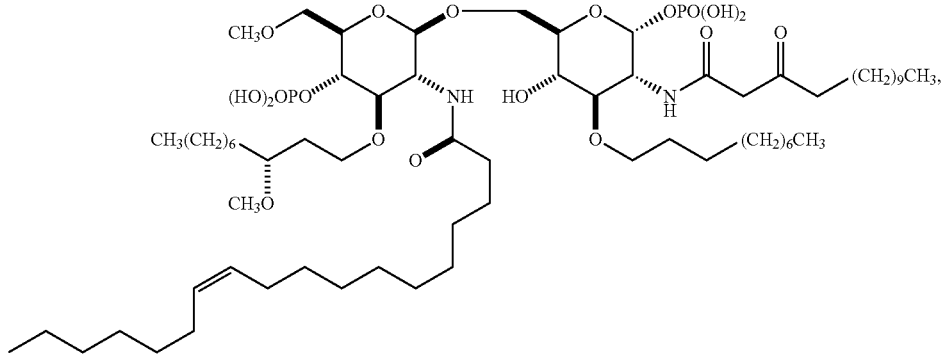

or a pharmaceutically acceptable salt thereof. This composition contains ≦0.1%, by weight, of any individual monosaccharide, such as a right or left side monosaccharide (as shown in formula set forth above), or ≦0.1%, by weight, of total monosaccharides.

The invention also includes a composition including E5564, or a pharmaceutically acceptable salt thereof, and ≦0.1%, by weight, of any individual dibutylphthalate, or ≦0.1%, by weight, of total dibutylphthalates.

An additional composition that is included in the invention contains E5564, or a pharmaceutically acceptable salt thereof, and ≦0.1%, by weight, of any individual disaccharide contaminant, or ≦0.1%, by weight, of total disaccharide contaminants. One or more of these disaccharide contaminants can include, for example, a modified β-ketoamide side chain, or can lack β-ketoamide side chain.

The invention further includes a composition containing E5564, or a pharmaceutically acceptable salt thereof; and ≦0.1%, by weight, of any particular impurity or all impurities. All of the compositions described herein can include a pharmaceutically acceptable carrier or diluent.

Also included in the invention are methods of obtaining compositions containing compound E5564, or a pharmaceutically acceptable salt thereof, and ≦0.1%, by weight, of a contaminant (e.g., the contaminants mentioned above). This method involves obtaining a preparation of the compound and subjecting the preparation to (i) anion exchange chromatography, (ii) preparative liquid chromatography, and (iii) solid phase extraction.

The invention also includes a method of preventing or treating endotoxemia in a patient by administering to the patient any of the compositions described herein, which include a pharmaceutically acceptable carrier or diluent. Patients that can be treated using the methods and compositions of the invention include, for example, surgical patients (e.g., cardiac surgical patients), if appropriate, patients that have or are at risk of developing endotoxemia, sepsis, or septic shock, patients that are infected with HIV, and patients who are immunocompromised due to their suffering from an immunological disorder. The invention further includes the use of the compositions described herein for preventing or treating these conditions, as well as for the preparation of medicaments for preventing or treating these conditions.

The invention provides several advantages. For example, the compositions and methods of the invention provide significant therapeutic benefits and the methods are easily carried out, especially with many of the patients treated according to the invention, who already may have intravenous lines inserted, as part of their treatment in the ICU. Also, because the compositions of the invention are highly pure, they enable the administration of lower amounts of drug preparation to patients than would be possible with a less pure preparation, to yield the same effect.

Other advantages of the invention will be apparent from the following detailed description, the drawings, and the claims.

DETAILED DESCRIPTION

The invention provides compositions that include a purified antiendotoxin compound and methods of preparing and using such compositions. In particular, the compositions of the invention include compound E5564, which has the formula:

β-ketoamide side chain). Alternatively, the compositions of the invention can include ≦0.1%, by weight, of any individual contaminant.

The compositions of the invention can be prepared using purification methods that are described in further detail below. Briefly, compound E5564 that has been obtained using, for example, the synthetic methods described in U.S. Pat. No. 5,681,824, is subjected to further purification steps, including anion exchange chromatography, preparative liquid chromatography, and solid phase extraction. Preferably, all three of these steps are carried out, in the order set forth above. However, as is understood in the art, these steps and their order can be varied, as long as compositions as described herein are obtained. In addition, as can be determined by those of skill in this art, any of these steps can be carried out at appropriate points during synthesis of the drug, rather than after synthesis, as is described below.

Figure 1:
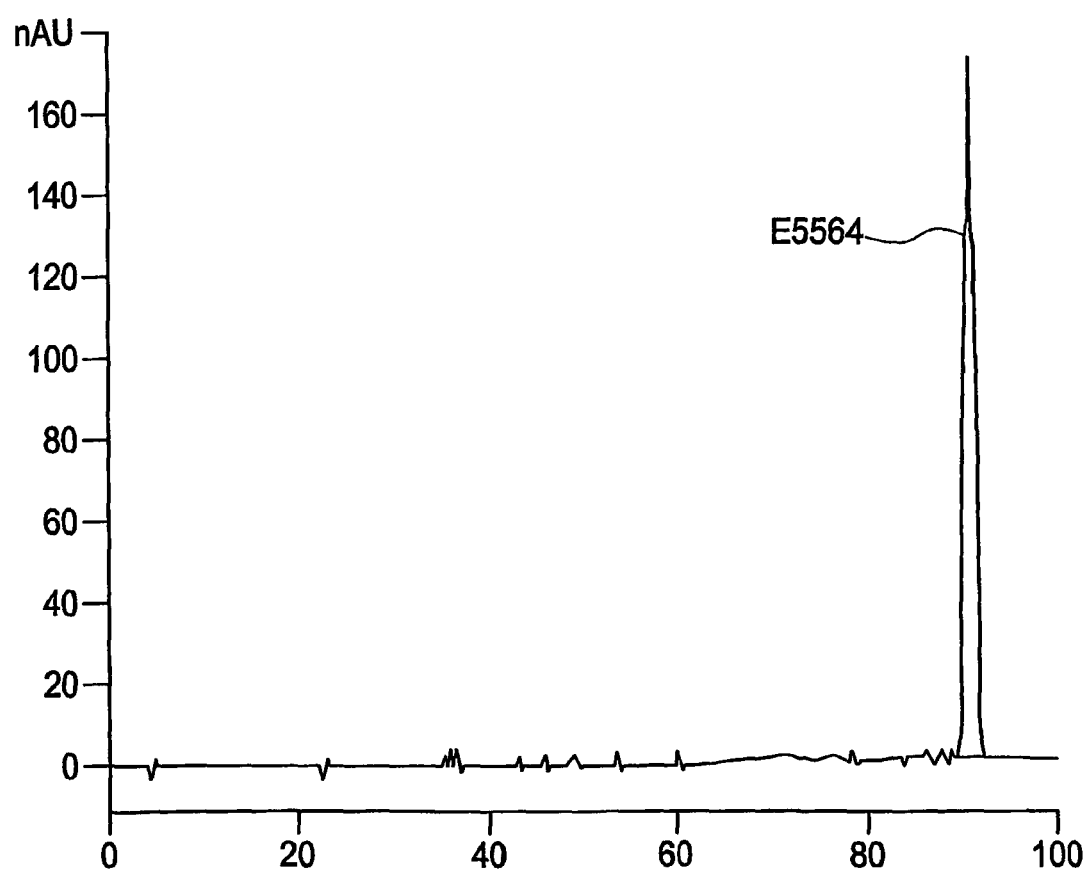
FIG. 1 is an HPLC chromatogram, full scale, of a preparation of compound E5564 prior to purification using the methods of the invention.
Figure 2:
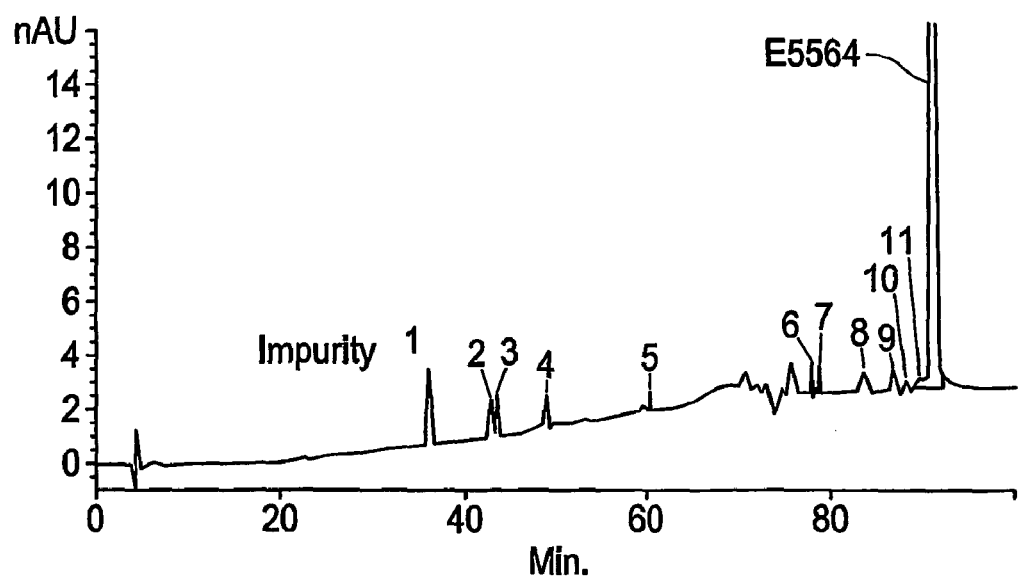
FIG. 2 is an HPLC chromatogram, expanded view, of a preparation of compound E5564 prior to purification using the methods of the invention.
Figure 3A:
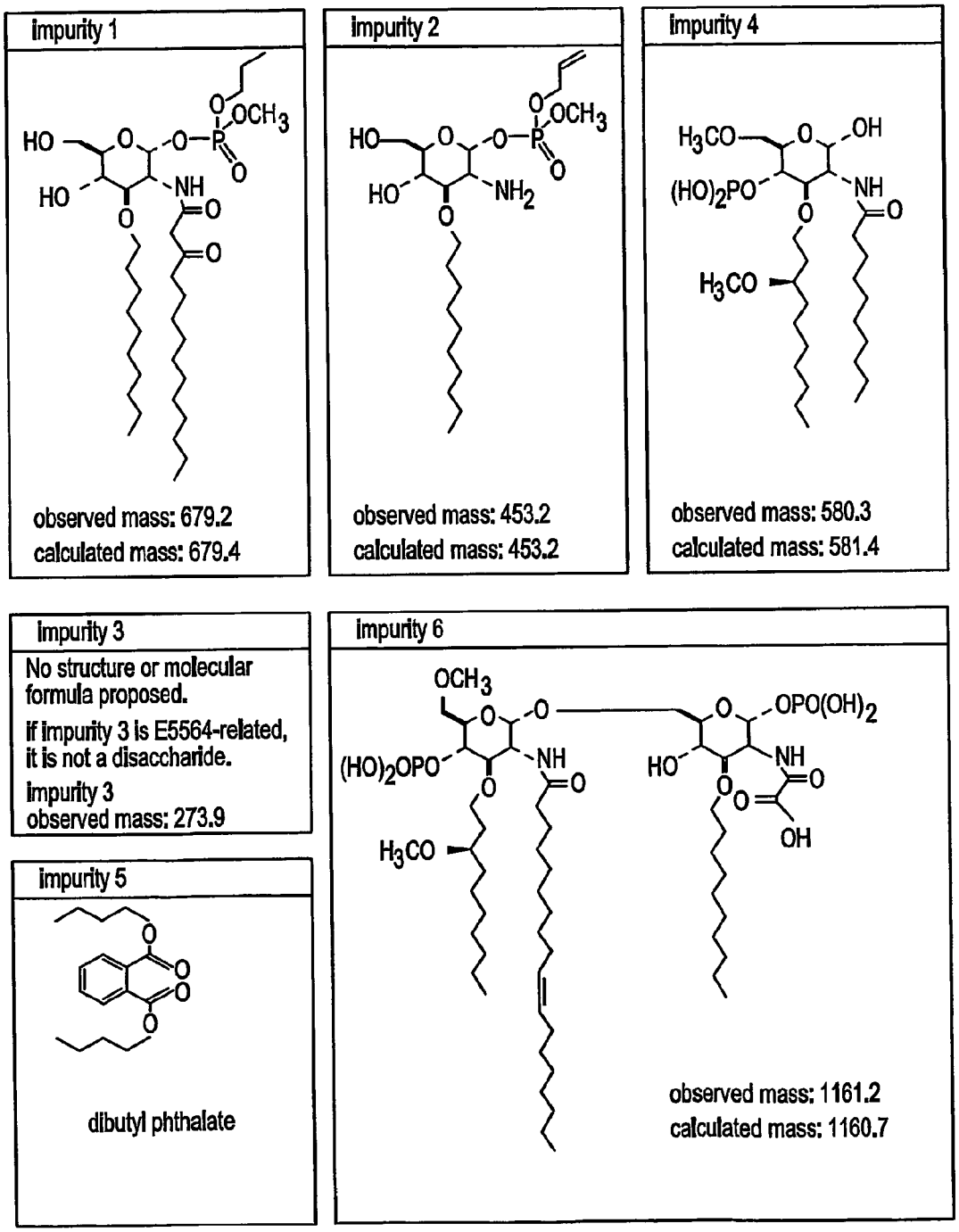
FIG. 3 is a schematic representation of compounds that may be present in the compositions of the invention.
Figure 3B:
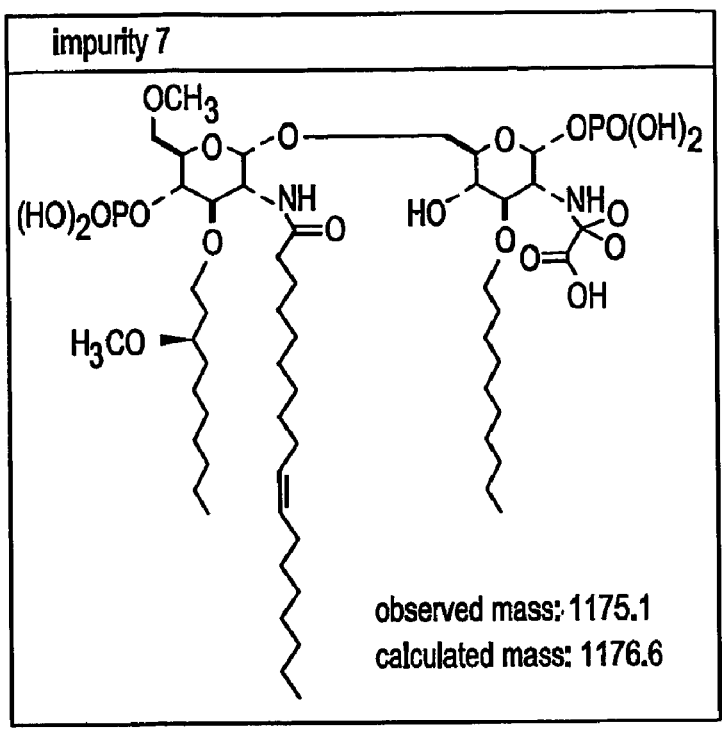
Figure 3B:
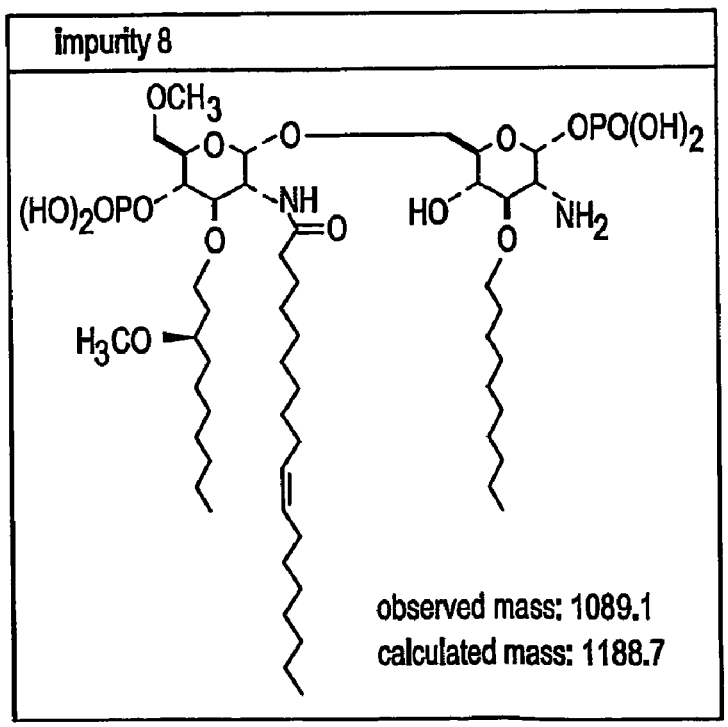
Figure 3C:
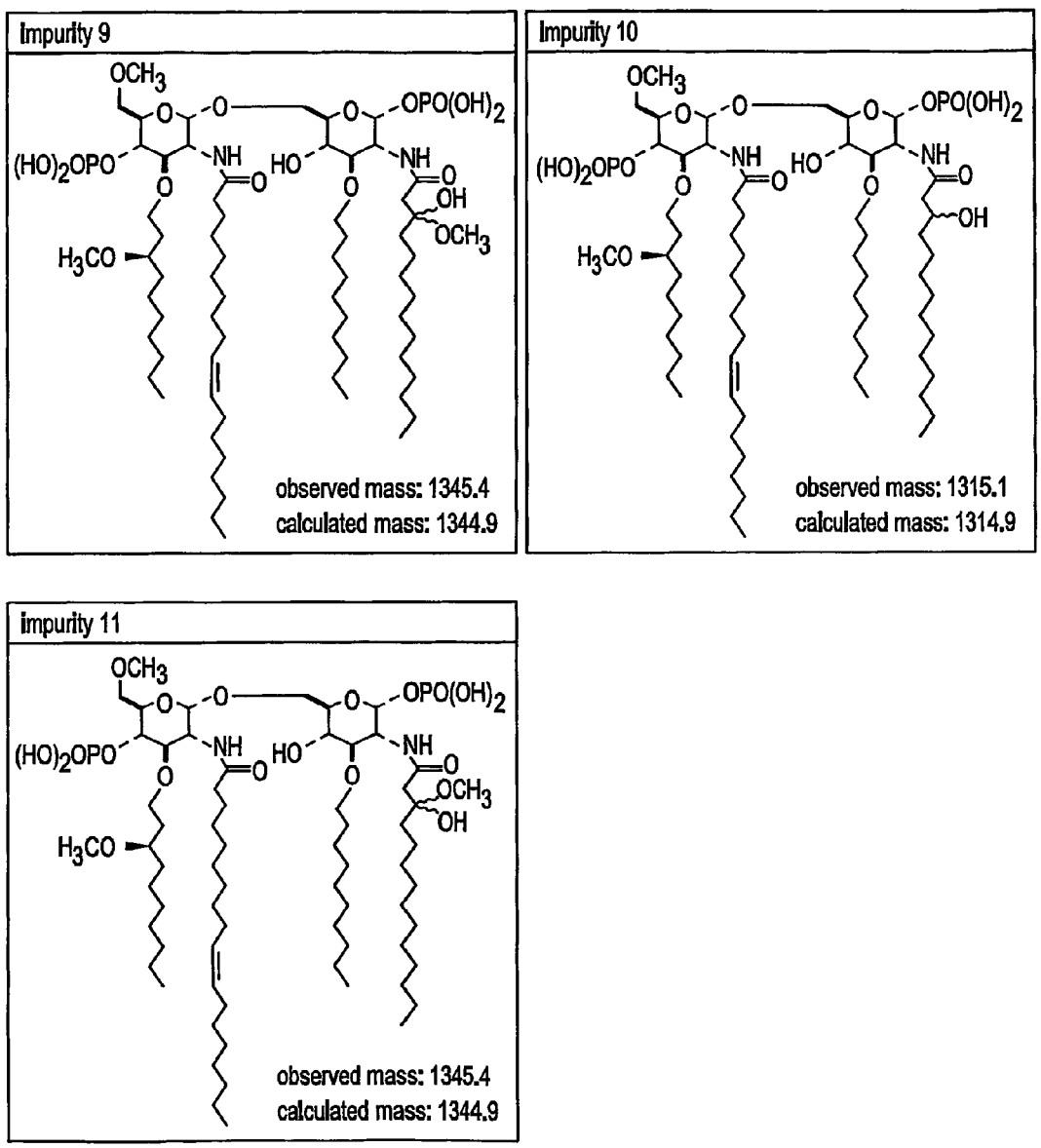

Purification of E5564 by Ion Exchange Chromatography, Liquid Chromatography, and Solid Phase Extraction Using Polystyrene-Based Stationary Phases As is noted above, compound E5564 can be obtained using the method described in U.S. Pat. No. 5,681,824. Fractionation of drug obtained using this method revealed that the preparation includes material in addition to the drug (FIGS. 1 and 2). In particular, a column having the following characteristics was used to carry out HPLC analysis of the drug: YMC ODS AP303, 4.6×250 mm, 5 μm particle size, 300 Å pore size. The injection volume was 25 μL, and the column was run at a flow rate of 0.8 mL/minute, at ambient temperature, and monitored at 254 nm UV absorbance. The mobile phases were A: 20/900/100 $H_3PO_4/H_2O/MeOH$, and B: 20/980 $H_3PO_4/MeOH$. The gradient used was 10% B: 0-10 minutes, 10-100% B: 10-70 minutes, and 100% B: 70-100 minutes. Structures of compounds that may be present in the drug preparation are shown in FIG. 3.

To purify the drug further, the crude reaction product, from concentration of the last chemical reaction, is dissolved in methanol containing at least 5% water. Typically, 4.5 kg of methanol/water is required to dissolve 2.9 kg of crude reaction concentrate. This solution is loaded onto a previously prepared column packed with a polystyrene-based, tetraalkyl ammonium-functionalized ion exchange resin, such as Source 30Q from Pharmacia Biotech. The size of the ideal load can be determined empirically or can be calculated from

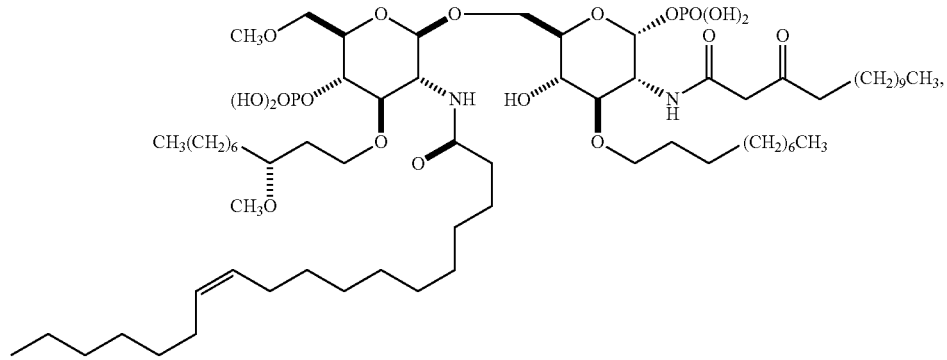

or a pharmaceutically acceptable salt thereof, and ≦0.1%, by weight, of any particular type of contaminant, such as a monosaccharide (e.g., a right or left side monosaccharide), a dibutylphthalate, or a disaccharide (e.g., a disaccharide that includes a modified β-ketoaraide side chain or that lacks a the load capacity of the resin and the moles of exchangeable functionality in the crude product solution. Initial purification begins by elution of non-charged reagents, impurities, and reaction by-products using methanol/water mixtures as a mobile phase. Typically, methanol containing at least 5% water is an effective mobile phase. The elution of non-product compounds is typically monitored using an in-line UV/vis detector. After removal of the non-charged species, E5564 is eluted and separated from the remaining charged impurities by using a mobile phase with an increasing salt gradient. The nature of the product salt form can be changed by varying the cation component of this salt gradient. Typically, a slow gradient from 95:5 (v/v) methanol:water to 95:5 (v/v) methanol:4.6 M NaOH is effective for initial purification of E5564 as the tetrasodium salt. Use of ammonium chloride for the salt gradient allows purification of E5564 as the tetraammonium salt. The separation and purification at this stage is easily monitored by in-line UV/vis detection and/or in-line conductivity detection. Individual fractions containing either E5564 or the various by-products are collected separately and can be held for isolation and/or further processing.

The product solution from the ion exchange initial purification is analyzed for product content and quality, and then is used directly as a feed solution for final purification using LC over a non-functionalized, polystyrenedivinylbenzene resin as the stationary phase, such as Source 15 RPC from Pharmacia Biotech. A portion of the product-containing solution from the ion exchange chromatography containing up to 60 g of E5564 free acid equivalent is loaded onto a previously prepared column containing 20-25 L of stationary phase. Purification is effected by elution with mobile phases containing methanol and water or methanol, water, and sodium hydroxide. Typically, the mobile phase uses a gradient, but may have extended isocratic portions. The exact composition is dependent upon the separation being effected. For example, a typical purification mobile phase is isocratic 95:5 (v/v) methanol:0.1 M NaOH for 20 minutes, followed by a gradient to 100% methanol over 15 minutes. Elution of the by-products and E5564 is monitored by using an in-line UV/vis detector. Fractions containing either by-products or pure E5564 are collected separately and can be isolated individually, combined with equivalent fractions from subsequent injections, or can be held for further processing.

Combined fractions of either pure E5564 or purified by-products containing up to 150 g free acid equivalent are typically diluted with water to a final solvent composition of 50:50 (v/v) methanol:water. This solution is loaded onto a column containing 20-25 L of a previously prepared polystyrenedivinylbenzene, non-functional resin, such as Source 15 RPC from Pharmacia Biotech, as a stationary phase. After loading, the mobile phase is changed gradually, through a gradient, from 50:50 methanol:water to 100% acetonitrile. During this step, no compounds elute from the column, but water is removed from the system. After elution with at least 1 column volume of acetonitrile, the mobile phase is changed through, preferably, a very steep gradient to 100% methanol. The purified compound elutes in a very concentrated band during this step. Elution of the purified compound is monitored by an in-line UV/vis detector. The resultant pure product solution has been concentrated by up to 10 times and the solution is now water free. This improves subsequent processing substantially. E5564, impurities, and reaction by-products can be purified effectively by the above-described technique.

To reduce the presence of impurities such as dibutylphthalates, the purification methods described above and/or the original synthesis can be carried out rising a limited amount of plastics, as dibutylphthalates are relatively ubiquitous plasticizers.

Use

As is noted above, the compositions of the invention can be used in methods for preventing and treating diseases and conditions associated with exposure to endotoxin. For use in these methods, the compositions of the invention are formulated to include pharmaceutically acceptable carriers or diluents. Standard methods for preparing and formulating drugs are well known in the art and can be used in the invention. For example, the drug, which can be stored as a freeze-dried formulation, can be dissolved in physiological saline (which may include 5% glucose). Alternatively, the drug can be formulated by dissolving 35.4 mg of drug substance in 52.1 ml 0.01 N NaOH, stirring for one hour at room temperature, and diluting into phosphate-buffered lactose. After adjusting the pH to 7.3 and diluting the drug to a final concentration of 0.1 mg/ml, the solution can be filter-sterilized and lyophilized. An example of a formulation of antiendotoxin drug product in 10 ml vials is shown below.

TABLE 1

| Material | amount |
|---|---|
| E5564 | 10 mg |
| $NaH_2PO_4 \cdot 4H_2O$ | qs |
| NaOH | qs |
| Lactose hydrous | 400 mg |
| $Na_2HPO_4 \cdot H_2O$ | 1.8 mg |
| sterile water | 4 ml |

Additional appropriate formulations can readily be determined by those of skill in this art (see, e.g., *Remington's Pharmaceutical Sciences* ($18^{th}$ edition), ed. A. Gennaro, 1990, Mack Publishing Company, Easton, Pa.).

The compositions and methods of the invention can be used to prevent or to treat any of a large number of diseases and conditions associated with septic shock or endotoxemia. For example, the compositions and methods of the invention can be used in conjunction with any type of surgery or medical procedure, when appropriate, that could lead to the occurrence of endotoxemia or related complications (e.g., sepsis or septic shock syndrome). As a specific example, the invention can be used in conjunction with cardiac surgery (e.g., coronary artery bypass graft, cardiopulmonary bypass, and/or valve replacement), transplantation (of, e.g., liver, heart, kidney, or bone marrow), cancer surgery (e.g., removal of a tumor), or any abdominal surgery (see, e.g., PCT/US01/01273).

Additional examples of surgical procedures with which the compositions and methods of the invention can be used, when appropriate, are surgery for treating acute pancreatitis, inflammatory bowel disease, placement of a transjugular intrahepatic portosystemic stent shunt, hepatic resection, burn wound revision, and burn wound escharectomy. The invention can also be used in conjunction with non-surgical procedures in which the gastrointestinal tract is compromised. For example, the invention can be used in association with chemotherapy or radiation therapy in the treatment of cancer. The compositions and methods of the invention can also be used in the treatment of conditions associated with HIV infection, trauma, or respiratory distress syndrome, as well as with immunological disorders, such as graft-versus-host disease or allograft rejection. Pulmonary bacterial infection and pulmonary symptomatic exposure to endotoxin can also be treated using the compositions and methods of the invention (see, e.g., PCT/US00/02173).

Administration of the compositions of the invention can be carried out using any of several standard methods including, for example, continuous infusion, bolus injection, intermittent infusion, inhalation, or combinations of these methods. For example, a mode of administration is by continuous intravenous infusion. In such an approach, the infusion dosage rate of the drug can be, for example, 0.001-0.5 mg/kg body weight/hour, more preferably 0.01-0.2 mg/kg/hour, and most preferably 0.03-0.1 mg/kg/hour, infused over the course of; for example, 12-100, 60-80, or about 96 hours. The infusion of the drug can, if desired, be preceded by a bolus injection; preferably, such a bolus injection is given at a dosage of 0.001-0.5 mg/kg. Preferably, the total amount of drug administered to a patient is 25-600 mg of drug, more preferably 35-125 mg, by infusion over a period of 60-100 hours. As activity in the hospital, and particularly the ICU, is often hectic, minor variations in the time period of infusion of the drugs may occur and are also included in the invention.

Additional modes of administration of E5564, according to the methods of the invention, include bolus or intermittent infusion. For example, the drug can be administered in a single bolus by intravenous infusion through, for example, a central access line or a peripheral venous line, or by direct injection, using a syringe. Such administration may be desirable if a patient is only at short-term risk for exposure to endotoxin, and thus does not need prolonged persistence of the drug. For example, this mode of administration may be desirable in surgical patients, if appropriate, such as patients having cardiac surgery, e.g., coronary artery bypass graft surgery and/or valve replacement surgery. In these patients, a single bolus infusion of, e.g., 0.10-15 mg/hour (e.g., 1-7 mg/hour or 3 mg/hour) of drug can be administered over a period of four hours prior to and/or during surgery. (Note that the amount of drug administered is based on an assumed average weight of a patient of 70 kg.) Shorter or longer time periods of administration can be used, as determined to be appropriate by one of skill in this art.

In cases in which longer-term persistence of active drug is desirable, for example, in the treatment of a condition associated with long-term exposure to endotoxin, such as during infection or sepsis, or in appropriate surgical situations in which it is determined that prolonged treatment is desirable, intermittent administration can be carried out. In these methods, a loading dose is administered, followed by either (i) a second loading dose and a maintenance dose (or doses), or (ii) a maintenance dose or doses, without a second loading dose, as determined to be appropriate by one of skill in this art.

The first (or only) loading dose can be administered in a manner similar to that described for the single bolus infusion described above. That is, for E5564 administration, 0.10-15 mg/hour (e.g., 3-7 mg/hour or 3 mg/hour) of drug can be administered to a patient over a period of four hours prior to surgery. If a second loading dosage is to be used, it can be administered about 12 hours after the initial loading dose, and can involve infusion of, e.g., 0.10-15 mg/hour (e.g., 1-7 mg/hour or 3 mg/hour) of drug over a period of; e.g., about two hours.

To achieve further persistence of active drug, a maintenance dose (or doses) of drug can be administered, so that levels of active drug are maintained in the blood of a patient. Maintenance doses can be administered at levels that are less than the loading dose(s), for example, at a level that is about ⅙ of the loading dose. Specific amounts to be administered in maintenance doses can be determined by a medical professional, with the goal that drug level is at least maintained. Maintenance doses can be administered, for example, for about 2 hours every 12 hours beginning at hour 24 and continuing at, for example, hours 36, 48, 60, 72, 84, 96, 108, and 120. Of course, maintenance doses can be stopped at any point during this time frame, as determined to be appropriate by a medical professional.

In the case of pulmonary bacterial infection or pulmonary symptomatic exposure to endotoxin, administration of the compositions of the invention can be effected by means of periodic bolus administration, by continuous, metered inhalation, or by a combination of the two. A single dose is administered by inhalation 1 µg-24 mg, for example, 5-150 µg, or, preferably, 10-100 µg of the drug. Of course, recalcitrant disease may require administration of relatively high doses, e.g., 5 mg, the appropriate amounts of which can be determined by one of skill in this art. Appropriate frequency of administration can be determined by one of skill in this art, and can be, for example, 1-4, for example, 2-3, times each day. Preferably, the drug is administered once each day. In the case of acute administration, treatment is typically carried out for periods of hours or days, while chronic treatment can be carried out for weeks, months, or even years.

Both chronic and acute administration can employ standard pulmonary drug administration formulations. Administration by this route offers several advantages, for example, rapid onset of action by administering the drug to the desired site of action, at higher local concentrations. Pulmonary drug formulations are generally categorized as nebulized (see, e.g., Flament et al., Drug Development and Industrial Pharmacy 21(20):2263-2285, 1995) and aerosolized (Sciarra, "Aerosols," Chapter 92 in *Remington's Pharmaceutical Sciences*, 16$^{th}$ edition (ed. A. Osol), pp. 1614-1628; Malcobnson et al., PSTT 1(9):394-398, 1998, and Newman et al., "Development of New Inhalers for Aerosol Therapy," in Proceedings of the Second International Conference on the Pharmaceutical Aerosol, pp. 1-20) formulations.

All patents and publications mentioned herein are incorporated herein by reference. Other embodiments are within the following claims.

What is claimed is:

1. A composition comprising a compound having the formula:

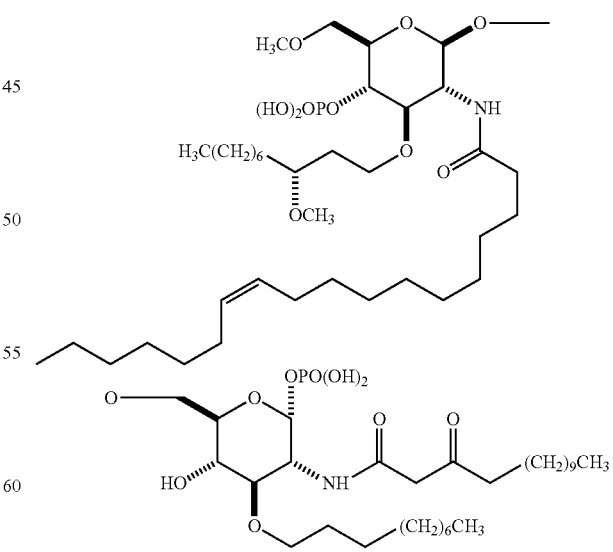

or a pharmaceutically acceptable salt thereof, said composition comprising ≦0.1%, by weight, of any individual monosaccharide.

2. The composition of claim 1, wherein said monosaccharide is a right side monosaccharide.

3. The composition of claim 1, wherein said monosaccharide is a left side monosaccharide.

4. The composition of claim 1, wherein said composition comprises ≦0.1%, by weight, of total monosaccharides.

5. The composition of claim 1, wherein said composition comprises ≦0.1%, by weight of any individual dibutylphthalate.

6. The composition of claim 1, wherein said composition comprising ≦0.1%, by weight, of any particular impurity.

7. The composition of claim 6, wherein said composition comprises ≦0.1%, by weight, total impurities.

8. The composition of claim 1, wherein the monosaccharide has the following structure:

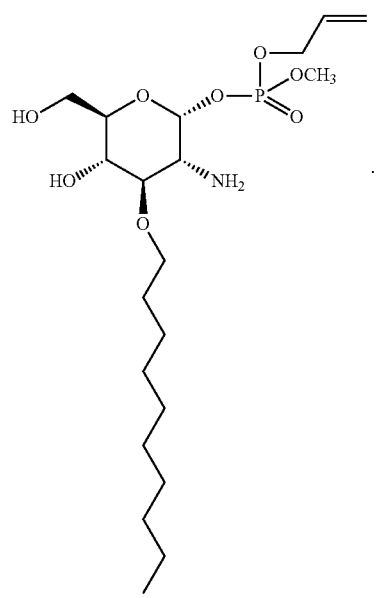 [SMILES: C=CCOP(=O)(OC)O[C@H]1O[C@H](CO)[C@@H](O)[C@H](OCCCCCCCCCC)[C@H]1N]

9. The composition of claim 1, wherein the monosaccharide has the following structure:

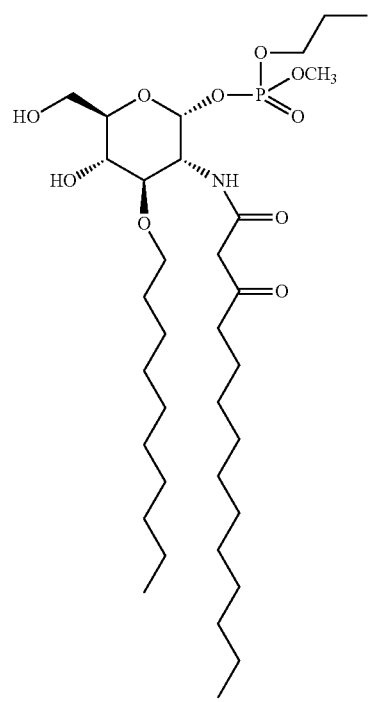

10. The composition of claim 1, wherein the monosaccharide has the following structure:

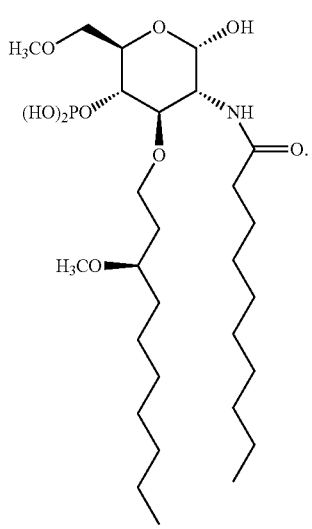

11. The composition of claim 1, further comprising a pharmaceutically acceptable carrier or diluent.

* * * * *